US010350422B2

(12) United States Patent
Sanders et al.

(10) Patent No.: US 10,350,422 B2
(45) Date of Patent: Jul. 16, 2019

(54) FEEDTHROUGH ASSEMBLY INCLUDING FERRULE WITH TAPERED EXTENSION(S)

(71) Applicant: Medtronic, Inc., Minneapolis, MN (US)

(72) Inventors: Matthew J. Sanders, Wayzata, MN (US); Paul B. Aamodt, Minnetonka, MN (US); Simon E. Goldman, St. Louis Park, MN (US); Scott J. Robinson, Forest Lake, MN (US); Brad C. Tischendorf, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/974,944

(22) Filed: May 9, 2018

(65) Prior Publication Data

US 2018/0353762 A1 Dec. 13, 2018

Related U.S. Application Data

(60) Provisional application No. 62/517,619, filed on Jun. 9, 2017.

(51) Int. Cl.
*H01G 4/35* (2006.01)
*A61N 1/375* (2006.01)
*H01R 13/52* (2006.01)

(52) U.S. Cl.
CPC ............. *A61N 1/3754* (2013.01); *H01G 4/35* (2013.01); *H01R 13/5202* (2013.01); *H01R 2201/12* (2013.01)

(58) Field of Classification Search
USPC ............................................. 174/539; 361/302
See application file for complete search history.

(56) References Cited

U.S. PATENT DOCUMENTS

| 3,304,362 | A | * | 2/1967 | August | ................... | C03C 29/00 |
| | | | | | | 148/431 |
| 3,538,464 | A | * | 11/1970 | Walsh | ................ | H01R 13/6315 |
| | | | | | | 333/182 |
| 4,053,692 | A | * | 10/1977 | Dey | ..................... | H01M 2/0202 |
| | | | | | | 429/171 |

(Continued)

OTHER PUBLICATIONS

U.S. Appl. No. 15/418,265, entitled "Medical Device Including Feedthrough Assembly", filed Jan. 27, 2017.

(Continued)

*Primary Examiner* — William H Mayo, III
*Assistant Examiner* — Krystal Robinson (57) ABSTRACT

In some examples, a feedthrough assembly a ferrule including a base portion and at least one projection extending from the base portion; a capacitive filter positioned adjacent the base portion of the ferrule such that an outer wall of the capacitive filter faces an inner wall of the at least one projection of the ferrule; a conductive pin extending through an aperture in the ferrule and an aperture in the capacitive filter; and an electrically conductive material between the inner wall of the at least one projection of the ferrule and outer wall of the capacitive filter that electrically couples the ferrule and the capacitive filter to ground the capacitive filter, wherein the inner wall of the at least one projection of the ferrule and the outer wall of the capacitive filter are tapered.

18 Claims, 5 Drawing Sheets

(56) References Cited

U.S. PATENT DOCUMENTS

| | | | | |
|---|---|---|---|---|
| 4,083,022 A * | 4/1978 | Nijman | H01R 13/7195 | 333/183 |
| 4,115,629 A * | 9/1978 | Dey | H01M 2/1282 | 429/56 |
| 4,233,372 A * | 11/1980 | Bro | H01M 2/08 | 429/174 |
| 4,308,323 A * | 12/1981 | Bowsky | H01M 2/08 | 429/174 |
| 4,314,213 A * | 2/1982 | Wakino | H01G 4/35 | 29/25.42 |
| 4,460,664 A * | 7/1984 | Jurva | H01M 2/065 | 429/181 |
| 4,991,582 A * | 2/1991 | Byers | A61N 1/375 | 228/124.6 |
| 5,287,076 A * | 2/1994 | Johnescu | H01R 13/719 | 333/182 |
| 5,333,095 A * | 7/1994 | Stevenson | A61N 1/3754 | 29/25.42 |
| 5,434,358 A * | 7/1995 | Glahn | H01L 23/10 | 174/551 |
| 5,440,447 A * | 8/1995 | Shipman | H01G 4/35 | 333/182 |
| 5,470,345 A * | 11/1995 | Hassler | A61N 1/375 | 257/E25.031 |
| 5,539,611 A * | 7/1996 | Hegner | C04B 37/026 | 174/152 GM |
| 5,620,476 A * | 4/1997 | Truex | A61N 1/3754 | 607/36 |
| 5,650,759 A * | 7/1997 | Hittman | A61N 1/3754 | 333/182 |
| 5,751,539 A * | 5/1998 | Stevenson | A61N 1/3754 | 174/143 |
| 5,782,891 A * | 7/1998 | Hassler | A61N 1/3758 | 607/36 |
| 5,866,851 A * | 2/1999 | Taylor | H01B 17/305 | 174/152 GM |
| 5,867,361 A * | 2/1999 | Wolf | H01G 9/10 | 361/302 |
| 5,905,627 A * | 5/1999 | Brendel | H01G 4/35 | |
| 5,959,829 A * | 9/1999 | Stevenson | H03H 1/0007 | 333/182 |
| 5,973,906 A * | 10/1999 | Stevenson | A61N 1/3754 | 361/302 |
| 5,998,733 A * | 12/1999 | Smith | C03C 29/00 | 174/152 GM |
| 5,999,398 A * | 12/1999 | Makl | H01G 4/35 | 338/20 |
| 6,008,980 A * | 12/1999 | Stevenson | H01G 4/35 | 361/302 |
| 6,414,835 B1 * | 7/2002 | Wolf | A61N 1/3754 | 361/302 |
| 6,529,103 B1 * | 3/2003 | Brendel | A61N 1/3754 | 333/182 |
| 6,545,854 B2 * | 4/2003 | Trinh | H01G 4/35 | 361/302 |
| 6,603,646 B2 * | 8/2003 | Anthony | H01G 4/012 | 257/E23.079 |
| 6,643,903 B2 | 11/2003 | Stevenson | | |
| 6,660,116 B2 | 12/2003 | Wolf | | |
| 6,768,629 B1 | 7/2004 | Allen | | |
| 6,882,248 B2 * | 4/2005 | Stevenson | A61N 1/3754 | 333/182 |
| 6,985,347 B2 * | 1/2006 | Stevenson | A61N 1/3752 | 361/302 |
| 7,210,966 B2 | 5/2007 | Taylor | | |
| 7,260,434 B1 | 8/2007 | Lim | | |
| 7,590,450 B2 | 9/2009 | Iyer | | |
| 7,668,597 B2 | 2/2010 | Engmark | | |
| 7,725,190 B2 | 5/2010 | Iyer | | |
| 7,957,806 B2 * | 6/2011 | Stevenson | A61N 1/3754 | 607/36 |
| 8,095,224 B2 * | 1/2012 | Truex | A61B 5/0031 | 607/115 |
| 8,160,707 B2 | 4/2012 | Iyer | | |
| 8,373,965 B2 | 2/2013 | Iyer | | |
| 8,468,664 B2 * | 6/2013 | Brendel | H01G 4/228 | 29/25.41 |
| 8,660,645 B2 * | 2/2014 | Stevenson | A61N 1/0556 | 361/302 |
| 8,751,002 B2 | 6/2014 | Kast et al. | | |
| 8,788,057 B2 * | 7/2014 | Stevenson | A61N 1/025 | 607/116 |
| 8,929,986 B2 * | 1/2015 | Parker | A61N 1/36071 | 607/36 |
| 8,982,532 B2 | 3/2015 | Iyer | | |
| 9,061,161 B2 | 6/2015 | Iyer | | |
| 9,220,916 B2 * | 12/2015 | Imran | A61N 1/375 | |
| 9,278,223 B2 | 3/2016 | Kast et al. | | |
| 9,345,895 B2 | 5/2016 | Iyer et al. | | |
| 9,427,596 B2 * | 8/2016 | Woods | A61N 1/3754 | |
| 2001/0050837 A1 | 12/2001 | Stevenson et al. | | |
| 2007/0123949 A1 * | 5/2007 | Dabney | A61N 1/3754 | 607/37 |
| 2007/0239223 A1 | 10/2007 | Engmark et al. | | |
| 2008/0049376 A1 * | 2/2008 | Stevenson | A61N 1/056 | 361/302 |
| 2012/0307416 A1 * | 12/2012 | Iyer | A61N 1/3754 | 361/302 |
| 2013/0060312 A1 * | 3/2013 | Iyer | H03H 7/0138 | 607/116 |
| 2013/0070387 A1 * | 3/2013 | Stevenson | H01G 4/35 | 361/302 |
| 2015/0165218 A1 | 6/2015 | Markham et al. | | |
| 2016/0126712 A1 | 5/2016 | Markham et al. | | |
| 2016/0263384 A1 | 9/2016 | Stevenson et al. | | |

OTHER PUBLICATIONS

C00015632.WOU3 (PCT/US2018/031791) PCT Notification of Transmittal of the International Search Report and the Written Opinion of the International Searching Authority, dated Aug. 9, 2018, 12 pages.

* cited by examiner

FEEDTHROUGH ASSEMBLY INCLUDING FERRULE WITH TAPERED EXTENSION(S)

CROSS-REFERENCE TO RELATED APPLICATIONS

This application claims the benefit of U.S. Provisional Patent Application 62/517,619 entitled "Feedthrough Assembly Including Ferrule with Tapered Extension(s)", filed on Jun. 9, 2017, which is incorporated herein by reference in its entirety.

TECHNICAL FIELD

The disclosure relates to electrical feedthroughs for implantable medical devices.

BACKGROUND

Electrical feedthroughs may provide an electrical pathway between an interior of a hermetically-sealed housing of an electronics device to a point outside the housing. For example, implantable medical devices (IMDs), such as implantable stimulation devices, implantable sensing devices, cardiac pacemakers, implantable cardioverter/defibrillators (ICDs) and neuromodulators, may use one or more electrical feedthroughs to make electrical connections between electrical circuitry within the implantable medical device and leads, electrodes, or sensors external to the device within a patient.

SUMMARY

In some examples, the disclosure is directed to feedthrough assemblies and techniques for forming feedthrough assemblies. The feedthrough assemblies may be used to provide electrical connections between an exterior of a housing of an IMD and an interior of the housing of the IMD. The feedthrough assemblies include a capacitive filter that, e.g., acts as a low-pass filter. An outer surface of the capacitive filter may be electrically coupled to a ferrule to ground the capacitive filter.

The ferrule may include a base portion and at least one projection (e.g., one or more fins) extending from the base portion. The capacitive filter may be positioned on the base of the ferrule such that an outer surface of the capacitive filter faces the inner surface of the at least one projection. To electrically couple the outer surface of the capacitive filter and inner surface of the projection(s) of the ferrule, electrically conductive material fills a gap between the inner surface of the projection(s) and outer surface of the capacitive filter, e.g., by reflowing a conductive solder into the gap. Compared to examples in which the inner surface of the ferrule projection(s) are parallel to the outer surface of the capacitive filter, the gap between the inner wall of the projection(s) of the ferrule and the outer wall of the capacitive filter decreases moving from a top of the at least one projection to the base portion of the ferrule. For example, the projection(s) may extend from the base of the ferrule in tapered fashion. In this manner, such feedthrough assemblies may allow for improved manufacturability, e.g., in terms of deposition of a thin film on the inner surface of the projection(s) and reflow of solder within the gap between ferrule projections and the capacitive filter.

In one aspect, the disclosure is directed to a feedthrough assembly including a ferrule including a base portion and at least one projection extending from the base portion; a capacitive filter positioned adjacent the base portion of the ferrule such that an outer wall of the capacitive filter faces an inner wall of the at least one projection of the ferrule; a conductive pin extending through an aperture in the ferrule and an aperture in the capacitive filter; and an electrically conductive material between the inner wall of the at least one projection of the ferrule and outer wall of the capacitive filter that electrically couples the ferrule and the capacitive filter to ground the capacitive filter, wherein the inner wall of the at least one projection of the ferrule and the outer wall of the capacitive filter are tapered relative to each other such that a gap between the inner wall of the at least one projection of the ferrule and the outer wall of the capacitive filter decreases moving from a top of the at least one projection to the base portion of the ferrule.

In another aspect, the disclosure is directed to an IMD including a housing defining an opening; and a feedthrough assembly disposed in the opening and attached to the housing, wherein the feedthrough assembly comprises a ferrule including a base portion and at least one projection extending from the base portion; a capacitive filter positioned adjacent the base portion of the ferrule such that an outer wall of the capacitive filter faces an inner wall of the at least one projection of the ferrule; a conductive pin extending through an aperture in the ferrule and an aperture in the capacitive filter; and an electrically conductive material between the inner wall of the at least one projection of the ferrule and outer wall of the capacitive filter that electrically couples the ferrule and the capacitive filter to ground the capacitive filter, wherein the inner wall of the at least one projection of the ferrule and the outer wall of the capacitive filter are tapered relative to each other such that a gap between the inner wall of the at least one projection of the ferrule and the outer wall of the capacitive filter decreases moving from a top of the at least one projection to the base portion of the ferrule, and wherein a hermetic seal is formed between the ferrule and the housing at the opening.

In another aspect, the disclosure is directed to a method for forming a feedthrough assembly, the method comprising positioning a capacitive filter adjacent a base portion of a ferrule such that an outer wall of the capacitive filter faces an inner wall of at least one projection extending from the base portion of the ferrule, the inner wall of the at least one projection of the ferrule and the outer wall of the capacitive filter are tapered relative to each other such that a gap between the inner wall of the at least one projection of the ferrule and the outer wall of the capacitive filter decreases moving from a top of the at least one projection to the base portion of the ferrule, wherein the filter assembly includes a conductive pin extending through an aperture in the ferrule and an aperture in the capacitive filter.

The details of one or more examples are set forth in the accompanying drawings and the description below. Other features, objects, and advantages of the disclosure will be apparent from the description and drawings, and from the claims.

DETAILED DESCRIPTION

As described above, examples of the disclosure relate to feedthrough assemblies. In some cases, example feedthrough assemblies may be employed to provide an electrical pathway between an interior of a hermetically-sealed housing of an electronics device to a point outside the housing. For example, implantable medical devices (IMDs), such as implantable stimulation devices, implantable sensing devices, cardiac pacemakers, and implantable cardioverter/defibrillators (ICDs) employ feedthrough assemblies to make electrical connections between electrical circuitry within the implantable medical device and leads, electrodes, or sensors external to the device within a patient. However, examples of the disclosure are not limited to such devices.

Figure 1:
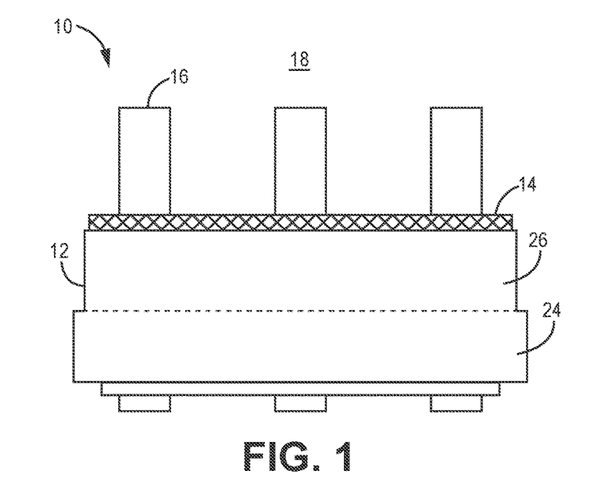
FIGS. 1-3 are diagrams illustrating front, side, and top views, respectively, an example feedthrough assembly in accordance with the disclosure.
Figure 2:
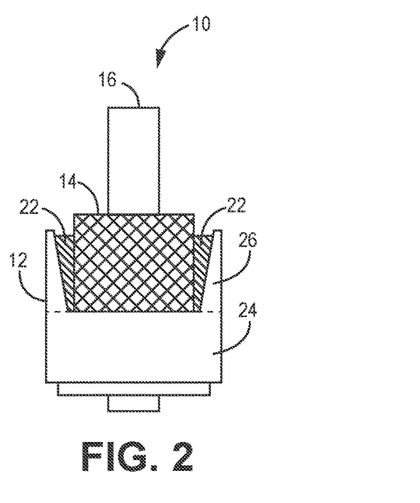
Figure 3:
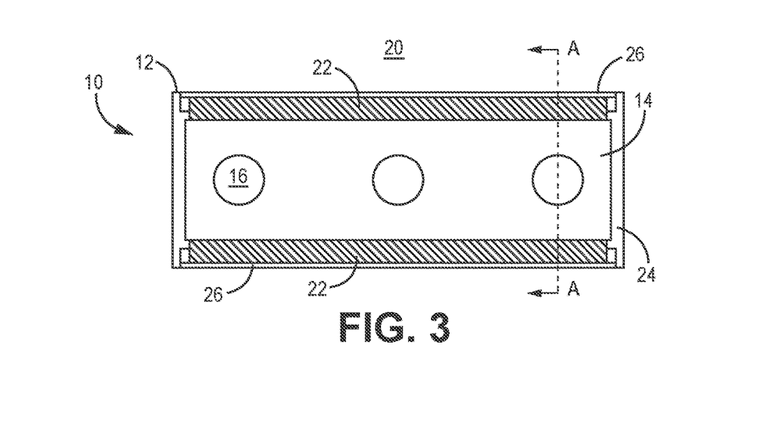
Figure 4:
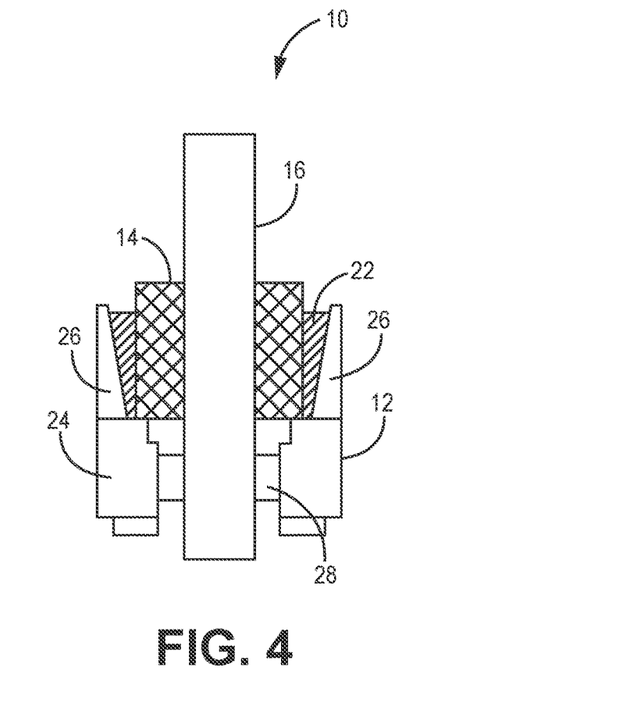
FIG. 4 is a diagram illustrating a cross-sectional view taken along lines A-A of FIG. 3.

FIG. 1 is a front view of an example feedthrough assembly 10. Feedthrough assembly 10 includes an internally-facing side 18 and an externally-facing side 20. FIG. 2 shows a side view of feedthrough assembly 10 of FIG. 1. FIG. 3 shows a top view of feedthrough assembly 10 showing the internally-facing side 18 of feedthrough assembly 10. FIG. 4 shows a cross-sectional view of feedthrough assembly 10 along cross-section A-A indicated in FIG. 3. The terms "internally-facing," "inwardly," and the like, when used herein with regards to feedthrough assembly 10, may generally refer to a direction toward the interior of an electronics device (e.g., an IMD) when assembly 10 is incorporated in the electronics device. Conversely, the terms "externally-facing," "outwardly," and the like, when used herein with regard to feedthrough assembly 10 generally refer to a direction toward the exterior of the electronics device when assembly 10 is incorporated in the electronics device.

As shown in FIGS. 1-4, feedthrough assembly 10 comprises a ferrule 12, feedthrough pin array (only pin 16 labeled in FIG. 1), and a capacitive filter 14. Ferrule 12 includes base portion 24 and projections 26 extending from base portion 24. FIG. 4 illustrates that respective feedthrough pins (e.g., pin 16) of the array extend from the internally-facing side 18 to the externally-facing side 20 of feedthrough assembly 10 through respective apertures in ferrule 12 and capacitive filter 14. Insulator 28 (e.g., a ceramic insulator such as glass) electrically isolates feedthrough pin 16 from ferrule 12 and may also provide a hermetic seal between internally-facing side 18 to the externally-facing side 20. Each feedthrough pin 16 is formed of an electrically conductive material provide a conductive pathway from the internally-facing side 18 to the externally-facing side 20 of feedthrough assembly 10, e.g., to deliver electrical stimulation or sense electrical signals in the case of an IMD or other medical device. While the example assembly 10 includes a feedthrough array with three feedthrough pins, any number of feedthrough pins in the feedthrough arrays is contemplated, such as, e.g., 9-pin or 11-pin arrays.

Ferrule 12 may be configured to be mounted to or within the housing of an electronics device, such as an IMD. In some examples, ferrule 12 may include a flange or other mechanical feature that facilitates mounting of ferrule 12 to or within the housing of the electronics device. Ferrule 12 may be mounted to the IMD housing, for example, by welding or brazing.

In one example, ferrule 12 comprises a material that facilitates mounting of ferrule 12 to the housing of an IMD. For example, the IMD housing may comprise titanium or a titanium alloy, and ferrule 12 may comprise titanium or a titanium alloy that can be welded to the IMD housing. Examples of materials from which ferrule 12 may be formed include niobium; titanium; titanium alloys such as titanium-6Al-4V or titanium-vanadium; platinum; molybdenum; zirconium; tantalum; vanadium; tungsten; iridium; rhodium; rhenium; osmium; ruthenium; palladium; silver; and alloys, mixtures, and combinations thereof.

Feedthrough assembly 10 may be employed in an IMD or other medical devices. Such electrical devices can, under some circumstances, be susceptible to electromagnetic interference (EMI) interfering with normal operation of circuitry within the IMD. As such, feedthrough assembly 10 includes capacitive filter 14 to address EMI. For example, capacitive filter 14 may be configured to act as a low-pass filter, transmitting relatively high frequency electromagnetic signals to ground (e.g., the housing of the IMD by way of ferrule 12) and passing relatively low frequency signals to circuitry within the IMD. Any suitable capacitive filter may be employed and may include a suitable monolithic ceramic capacitive filter.

Feedthrough assembly 10 includes electrically conductive material 22 that electrically couples ferrule 12 to capacitive filter 14 to ground filter 14. For example, electrically conductive material 22 may be in contact with plating on the outer surface of filter 14 that are electrically couple to one or more conductive plates within the filter 14 that are configured to be ground. Additionally, the electrically conductive material 22 may also mechanically couple ferrule 12 to capacitive filter 14. As shown in FIG. 2, e.g., electrically conductive material 22 is located between ferrule projections 26 and capacitive filter 14. Electrically conductive material 22 may be any suitable solder. As described further below, electrically conductive material 22 may be deposited as shown in FIG. 2 by reflowing a solder paste, ribbon or other suitable material into the gap between the inner surface of projection 26 and opposing outer surface of filter 14. Any suitable solder material may be used, such as, e.g., a tin lead solder.

Figure 5:
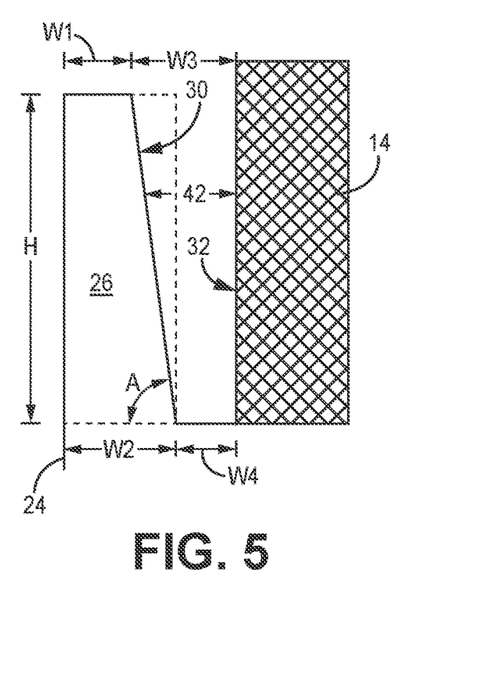
FIG. 5 is a diagram illustrating an example of a tapered ferrule projection adjacent a capacitive filter of the example feedthrough assembly of FIGS. 1-3.

FIG. 5 is a magnified view of feedthrough assembly 10 of FIGS. 1-3 showing one of the projections 26 (the left side projection 26 shown in FIG. 2) extending from ferrule base portion 24 to a height H at the top of projection 26 as well as showing a portion of adjacent capacitor filter 14. For purposes of description, the view of assembly 10 is shown in FIG. 5 without electrically conductive material 22 within gap 42 between inner surface 30 and outer surface 32 of capacitive filter 14.

As shown in FIG. 5, inner wall 30 of projection 26 and outer wall 32 of capacitive filter 14 are tapered relative to each other such that gap 42 between inner wall 30 of projection 26 and outer wall 32 of capacitive filter 14 decreases moving from the top of the at least one projection to base portion 24 of the ferrule 12. For example, as shown in FIG. 5, projection 26 is tapered such that inner wall 30 tapers from width W2 adjacent base portion 24 of ferrule 12 to a lesser width W1 at the top of projection 26. The taper of inner wall 30 may be expressed term of angle A shown in FIG. 5, which is less than 90 degrees. With outer wall 32 of capacitive filter 14 being substantially perpendicular to upper surface of base portion 24 of ferrule 12, the width of gap 42 decreases from W3 adjacent the top of projection 26 to W4 at the surface of base portion 24.

In some aspects, inner surface 30 of projection 26 and outer surface 32 of filter 14 may be described as being non-parallel to each other, e.g., compared to an instance in which inner surface 30 extends from base portion 26 in accordance with the dashed line shown in FIG. 5 such that inner surface 30 of projection 26 and outer surface 32 of filter 14 are parallel to each other.

Figure 8:
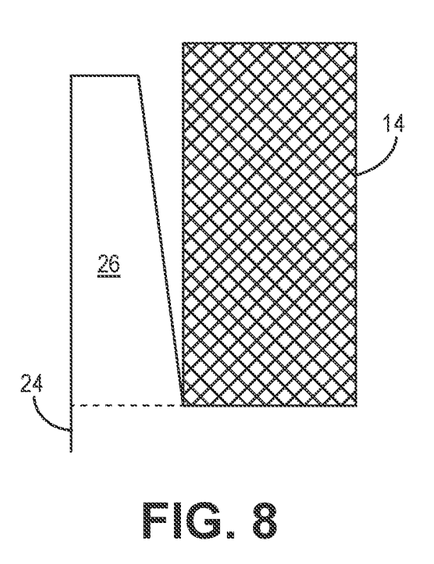
FIG. 8 is a diagram illustrating another example of a tapered ferrule projection adjacent a capacitive filter in accordance with the disclosure.

Any suitable values may be selected for the parameters shown in FIG. 5 (e.g., W1, W2, W3, W4, H, and angle A), which may be dependent on the overall design of feedthrough assembly 10 as well as the electronic device in which assembly 10 will be employed. Width W1 may be about 1 mils to about 20 mils, such as, e.g., about 5 mils. Width W2 may be greater than W1 and may be about 5 mils to about 30 mils, such as, e.g., about 15 mils. Height H may be about 25 mils to about 60 mils, such as, e.g., about 40 mils to about 60 mils or about 50 mils. Width W3 may be selected based on the dimensions of the solder preform used for reflow (e.g., W3 is selected so the reflow may be seated at least particular within the top gap having a width of W3). W3 may be about 2 mils to about 20 mils. Width W4 may be greater than zero, such as, e.g., about 2 mils, or may be zero (e.g., without a gap between inner surface 30 and outer surface 32 at the base portion 24 as shown in FIG. 8). Angle A may be less than 90 degrees, such as, e.g., about 80 degrees to about 84 degrees. Other values than those described above for each of the parameters are contemplated.

Figure 6:
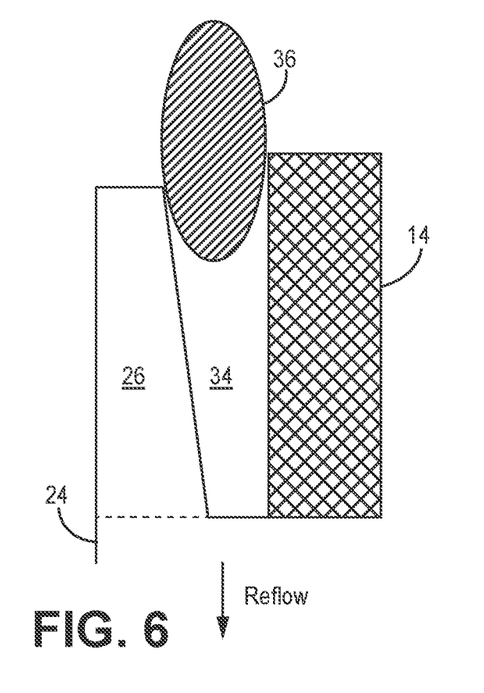
FIGS. 6 and 7 are diagrams that illustrates reflow of solder into a gap between the capacitive filter and tapered ferrule projection of FIG. 5.
Figure 7:
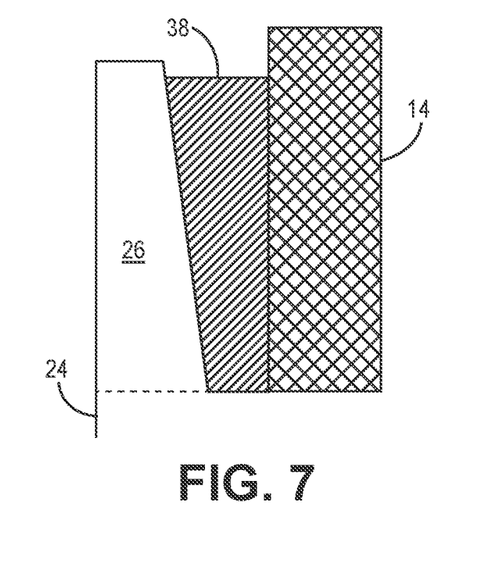

Examples of the disclosure may be manufactured using any suitable techniques. As shown in FIGS. 6 and 7, a solder material, e.g., a solder ribbon may be placed/seated in the upper gap between the top of projection 26 and outer wall 32 of filter 14. In such a configuration, empty cavity 34 is defined between projection 26 and filter 14. The solder material may be reflowed into empty cavity 34, e.g., in an inert atmosphere, to form solder 38 that electrically couples ferrule 12 and filter 14 to ground filter 14.

In some examples, prior to the reflow process, a thin film may be deposited onto the inner surface 30 of projection 22 using any suitable deposition technique. The thin film may be deposited prior to positioning filter 14 adjacent to projection 26 and may improve the wetting of the solder during reflow. Such a thin film may be employed when the solder material does not adequately wet to the inner surface 30 of projection, e.g., based on the composition of ferrule 12.

The tapered nature of projection 26, tapered nature of gap 42, and/or non-parallel orientation of inner surface 30 of projection 26 and outer surface 32 may improve the manufacturability of feedthrough assembly 10, e.g., in terms of depositing a thin film on inner surface 30 and adequately grounding capacitive filter 14 as described herein. As first example, the tapered configuration of projection 26 improves thin film application techniques by having a non-perpendicular face of inner surface 30 for line of sight processes (e.g., sputter deposition). For example, the overall thickness of such a thin film may be increased and/or the rate at which the thin film increases in thickness may be increased. As a second example, a void volume such as empty cavity 34 in FIG. 6 may be available for solder placement even when width W4 is zero as a result of the tapered nature of projection 26 and/or tapered nature of gap 42. As a result of the first example and the second example, the solder 38 achieves a high area of coverage between inner surface 30 of projection 26 and outer surface 32 of filter 14.

Thus, the grounding of filter 14 may be improved or at a desirable level, which may provide desirable loss performance for the high voltage pins of the feedthrough array of assembly 10. In some examples, insertion loss may be improved by incorporating examples assemblies of the present disclosure.

Figure 9:
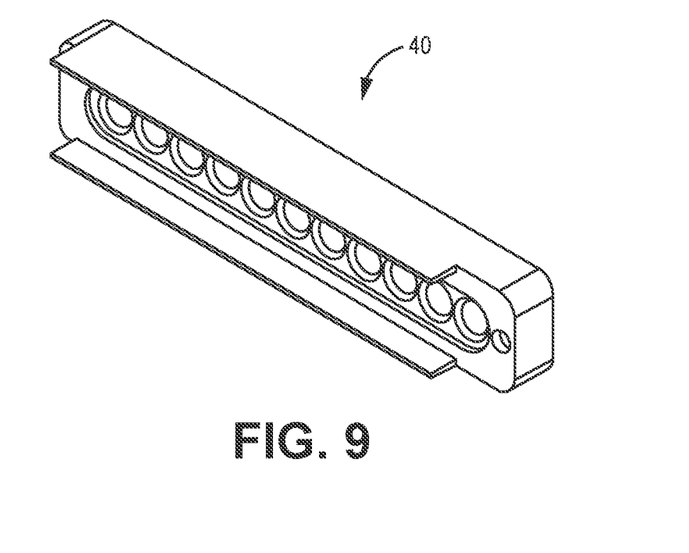
FIGS. 9 and 10 are diagrams illustrating views an example ferrule with tapered projections (or "fins") for an example feedthrough assembly including a 11-pin array.
Figure 10:
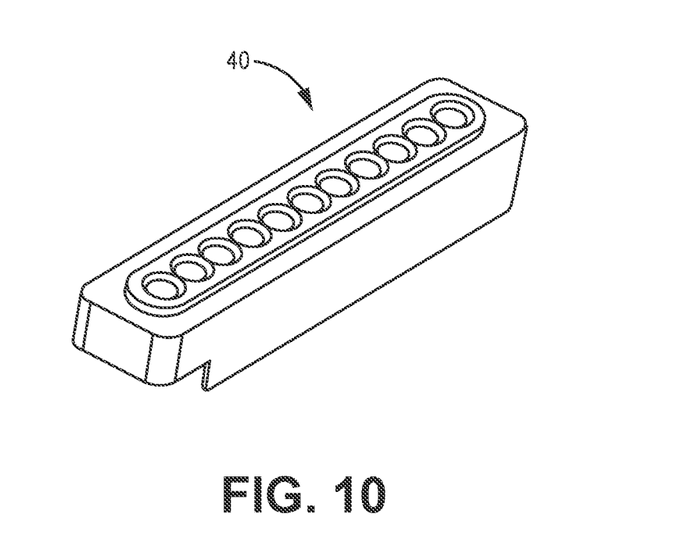

As noted above, while assembly 10 describes herein included a 3-pin feedthrough array, examples are not limited as such. For example, FIGS. 9 and 10 illustrate ferrule 40 having two tapered projections (also referred to as tapered fins) that may be employed in the manner describes herein for an assembly including an 11-pin feedthrough array.

While the example assembly 10 described herein include a ferrule 12 that included two tapered projections (also referred to as tapered fins), examples are not limited as such. For example, a ferrule may include one tapered projection or more than two tapered projections. In some examples, the ferrule may include a single continuous tapered projection that either fully or partially surround the outer wall of an adjacent capacitive filter, e.g., as an elongated circle or horseshoe shape.

Various examples have been described. These and other examples are within the scope of the following claims.

The invention claimed is:

1. A feedthrough assembly comprising:
a ferrule including a base portion and at least one projection extending from the base portion;
a thin film on the inner wall of the at least one projection of the ferrule configured to wet a solder during reflow;
a capacitive filter positioned adjacent the base portion of the ferrule such that an outer wall of the capacitive filter faces an inner wall of the at least one projection of the ferrule;
a conductive pin extending through an aperture in the ferrule and an aperture in the capacitive filter; and
an electrically conductive material between the inner wall of the at least one projection of the ferrule and outer wall of the capacitive filter that electrically couples the ferrule and the capacitive filter to ground the capacitive filter,
wherein the inner wall of the at least one projection of the ferrule and the outer wall of the capacitive filter are tapered relative to each other such that a gap between the inner wall of the at least one projection of the ferrule and the outer wall of the capacitive filter decreases moving from a top of the at least one projection to the base portion of the ferrule.

2. The assembly of claim 1, wherein the at least one projection extending from the base portion is tapered such that a width of the at least one projection increases moving from a top of the at least one projection to the base portion of the ferrule.

3. The assembly of claim 1, wherein the at least one projection extending from the base portion is tapered such the inner wall extends from the base portion of the ferrule at an angle greater than 90 degrees.

4. The assembly of claim 1, wherein the electrically conductive material comprises a solder reflow.

5. The assembly of claim 1, wherein the at least one projection of the ferrule includes a first fin projection having an inner wall facing a first portion of the outer wall of the capacitive filter and a second fin projection having an inner wall facing a second portion of the outer wall of the capacitive filter.

6. The assembly of claim 5, wherein the first fin projection and a second fin projections are tapered such that a width of each of the fin projections increases moving from respective tops of the fin projections to the base portion of the ferrule.

7. The assembly of claim 1, wherein the at least one projection comprises a single continuous projection.

8. The assembly of claim 7, wherein the single continuous projection surrounds the capacitive filter.

9. The assembly of claim 7, wherein the single continuous projection partially surrounds the capacitive filter.

10. An implantable medical device comprising:
a housing defining an opening; and
a feedthrough assembly disposed in the opening and attached to the housing, wherein the feedthrough assembly comprises:
  a ferrule including a base portion and at least one projection extending from the base portion;
  a capacitive filter positioned adjacent the base portion of the ferrule such that an outer wall of the capacitive filter faces an inner wall of the at least one projection of the ferrule;
a thin film on the inner wall of the at least one projection of the ferrule configured to wet a solder during reflow;
a conductive pin extending through an aperture in the ferrule and an aperture in the capacitive filter; and
an electrically conductive material between the inner wall of the at least one projection of the ferrule and outer wall of the capacitive filter that electrically couples the ferrule and the capacitive filter to ground the capacitive filter,
wherein the inner wall of the at least one projection of the ferrule and the outer wall of the capacitive filter are tapered relative to each other such that a gap between the inner wall of the at least one projection of the ferrule and the outer wall of the capacitive filter decreases moving from a top of the at least one projection to the base portion of the ferrule, and
wherein a hermetic seal is formed between the ferrule and the housing at the opening.

11. The device of claim 10, wherein the at least one projection extending from the base portion is tapered such that a width of the at least one projection increases moving from a top of the at least one projection to the base portion of the ferrule.

12. The device of claim 10, wherein the at least one projection extending from the base portion is tapered such the inner wall extends from the base portion of the ferrule at an angle greater than 90 degrees.

13. The device of claim 10, wherein the electrically conductive material comprises a solder reflow.

14. The device of claim 10, wherein the at least one projection of the ferrule includes a first fin projection having an inner wall facing a first portion of the outer wall of the capacitive filter and a second fin projection having an inner wall facing a second portion of the outer wall of the capacitive filter.

15. The device of claim 14, wherein the first fin projection and a second fin projections are tapered such that a width of each of the fin projections increases moving from respective tops of the fin projections to the base portion of the ferrule.

16. The device of claim 10, wherein the at least one projection comprises a single continuous projection.

17. The device of claim 16, wherein the single continuous projection surrounds the capacitive filter.

18. The device of claim 16, wherein the single continuous projection partially surrounds the capacitive filter.

* * * * *